United States Patent [19]

Rousseau et al.

[11] 3,971,777

[45] July 27, 1976

[54] NOVEL STEROIDS AND THEIR USE

[75] Inventors: Geneviéve Rousseau, Paris; Vesperto Torelli, Maisons-Alfort, both of France

[73] Assignee: Roussel-UCLAF, Paris, France

[22] Filed: Sept. 8, 1975

[21] Appl. No.: 611,126

[30] Foreign Application Priority Data

Sept. 18, 1974 France .............................. 74.31501

[52] U.S. Cl. ........................ 260/239.5; 260/397.47; 260/397.5; 424/241; 260/239.55 R
[51] Int. Cl.² ......................................... C07J 33/00
[58] Field of Search ............ 260/239.5, 397.4, 397.5

*Primary Examiner*—Elbert L. Roberts
*Attorney, Agent, or Firm*—Hammond & Littell

[57] ABSTRACT

Novel (17α)-steroids derivatives optical active isomers or mixtures thereof of the formula

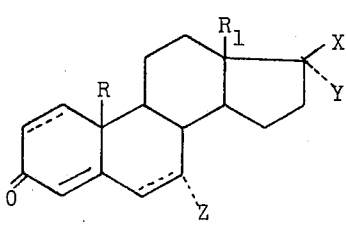

I wherein R is selected from the group consisting of hydrogen and methyl, $R_1$ is alkyl of 1 to 4 carbon atoms, Z is selected from the group consisting of hydrogen and

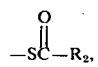

of α-configuration; $R_2$ is alkyl of 1 to 4 carbon atoms, the dotted lines in the A and B rings represent optional 1 or 2 double bonds in the 1(2) position when R is methyl and in the 6(7) position when Z is hydrogen and X and Y together form the group

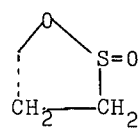

and when X is OH, Y is

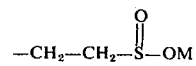

and M is selected from the group consisting of hydrogen, $-NH_4$ and alkali metals which have antialdosteronic activity and their preparation.

24 Claims, No Drawings

NOVEL STEROIDS AND THEIR USE

OBJECTS OF THE INVENTION

It is an object of the invention to provide the novel compounds of formula I as racemates or in optically active isomeric form.

It is another object of the invention to provide a novel process for the preparation of the compounds of formula I.

It is another object of the invention to provide novel antialdosterone compositions and to provide a novel method of treating arterial hypertension and cardiac insufficiency in warm-blooded animals.

These and other objects and advantages of the invention will become obvious from the following detailed description.

THE INVENTION

The novel steroids of the invention are racemates or optically active compounds of the formula

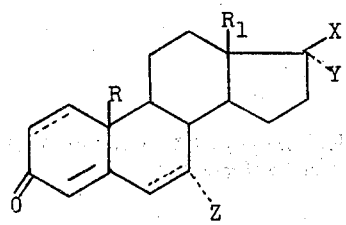

I wherein R is selected from the group consisting of hydrogen and methyl, $R_1$ is alkyl of 1 to 4 carbon atoms, Z is selected from the group consisting of hydrogen and

of α-configuration, $R_2$ is alkyl of 1 to 4 carbon atoms, the dotted lines in the A and B rings represent optional 1 or 2 double bonds in the 1(2) position when R is methyl and in the 6(7) position when Z is hydrogen and X and Y together form the group

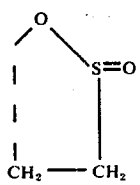

and when X is OH, Y is

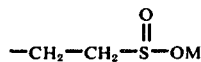

and M is selected from the group consisting of hydrogen, $-NH_4$ and alkali metals.

Among the preferred compounds of formula I, $R_1$ is preferably methyl, ethyl or n-propyl when R is hydrogen and when R is methyl, $R_1$ is preferably methyl. In the most preferred compounds, $R_1$ is methyl. $R_2$ is preferably methyl or ethyl. When M is alkali metal, it is preferably sodium, potassium or lithium.

Also among the preferred compounds are those where X and Y together form the group

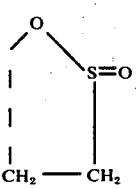

Among these compounds are those having only a double bond in the 4(5) position and Z is hydrogen or those having two double bonds in the 1(2) and 4(5) positions and Z is hydrogen or those having two double bonds in the 4(5) and the 6(7) positions and Z is hydrogen as well as those having a single double bond in the 4(5) position, Z is

and $R_3$ is alkyl of 1 to 4 carbon atoms.

Equally important compounds of formula I are those where X is —OH and Y is

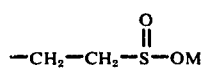

in which M is a defined above. Particularly important are those having a single double bond in the 4(5) position and M and Z are hydrogen.

Among the preferred compounds of formula I are potassium $\Delta^4$-(17α)-pregnene-17ol-3-one-21-sulfinate; $\alpha^4$-(17α)-pregnene-17-ol-3-one-21-sulfinic acid, 19-nor-$\Delta^4$-(17α)-pregnene-17-ol-3-one-21-sulfinic acid, $\Delta^{4,6}$-(17α)-pregnadiene-17-ol-3-one-21-sulfinic acid, $\Delta^{1,4}$-(17α)-pregnadiene-17-ol-3-one-21-sulfinic acid, 7-α-acetylthio-$\Delta^4$-(17α)-pregnene-17-ol-3-one-21-sulfinic acid, 19-nor-$\Delta^{4,6}$-(17α)-pregnadiene-17-ol-3-one-21-sulfinic acid and $\Delta^4$-(17α)-pregnene-17-ol-3-one-21-sulfinic acid and the sultines thereof either in their optically active isomeric form or as racemic mixtures thereof.

The novel process of the invention for producing the compounds of formula I where X and Y form the group

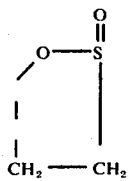

comprising reacting a compound of the formula

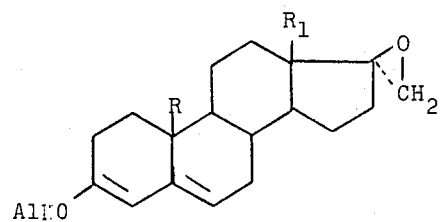

wherein Alk is alkyl of 1 to 4 carbon atoms with a methyl tertbutyl sulfoxide in the presence of butyllithium to form a compound of the formula

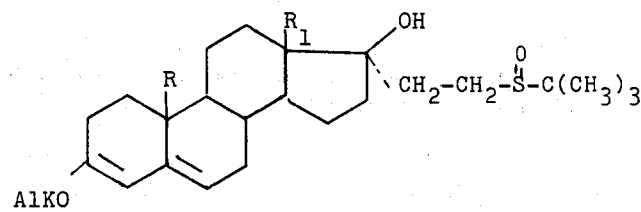

in the form of a mixture of diastereoisomers on the level of the sulfur atom which can be separated into the individual diastereoisomers and then reacting either one or the mixture of diastereoisomers with an acid hydrolysis agent to obtain the compounds of the formula

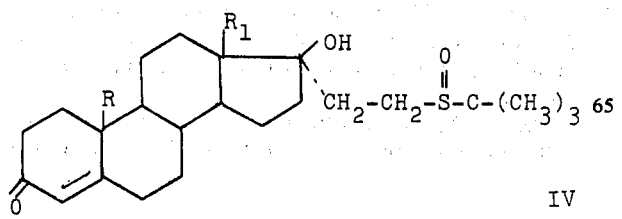

then reacting either one or the mixture of diastereoisomers with a member of the group consisting of N-chlorosuccinimide, N-bromo-succinimide and thionyl chloride to obtain a compound of the formula Ia in the form of a diastereoisomer or of a mixture of diastereoisomers which can be separated into the individual diastereoisomers, then each of them can be reacted with an alkyl orthoformate of the formula $$H-C-(OAlK_1)_3 \qquad V$$

wherein $AlK_1$ is alkyl of 1 to 4 carbon atoms to obtain a compound of the formula

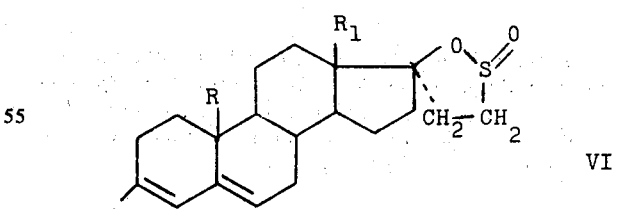

VI in the form of one of its diastereoisomers and reacting the latter with a deshydrogenation agent to obtain a compound of the formula

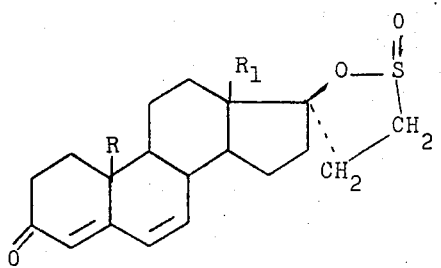   Ib which if desired may be reacted with a thioalkanolic acid of the formula

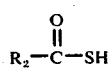   VIII wherein $R_2$ has the above definition to obtain a compound of the formula

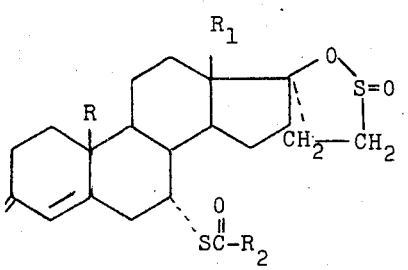   Ic or reacting a compound of formula IV with a deshydrogenation agent to obtain a compound of the formula reacting the latter with a member of the group consisting of thionyl chloride, N-chlorosuccinimide and N-bromosuccinimide to obtain a compound of the formula

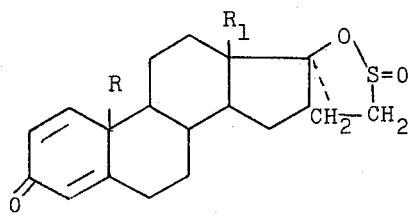   Id which may be reacted with a deshydrogenation agent to form a compound of the formula

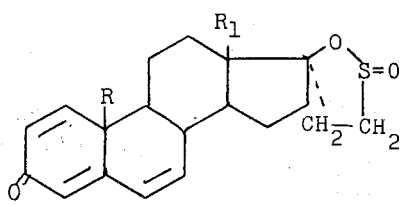   Ie

In the said process, AlK is preferably methyl, ethyl, n-propyl or n-butyl. The hydrolysis agent is preferably an acid such as hydrochloric acid, sulfuric acid, acetic acid, citric acid or p-toluenesulfonic acid. The hydrolysis can be effected in one or more solvents such as alcohols like methanol, ethanol or isopropanol, ketones such as acetone or a hydrocarbon such as benzene or toluene.

The agent for the formation of the sultine is preferably N-bromo-succinimide or N-chloro-succinimide. The thioalkanoic acid is preferably an acid wherein $R_2$ is methyl, ethyl, n-propyl or n-butyl.

The deshydrogenation agent used in the reaction with a compound of formula VI to produce a com-

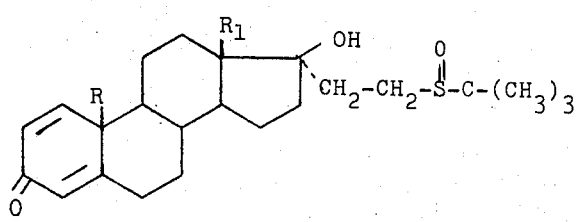   VIII pound of formula $I_b$ and with a compound of formula $I_d$ to produce a compound of formula $I_e$ is preferably chloranil although other derivatives of benzoquinone such as 2,3-dichloro-5,6-dicyanobenzoquinone may also be used. The alkyl orthoformate is preferably methyl, ethyl or n-propyl orthoformate and the reaction is preferably effected in a lower alkanol such as methanol or ethanol. The change of the compound of formula IV into a compound of formula VIII is preferably effected by a biochemical method.

A modification of the process of the invention for the production of compounds of formula I wherein X is OH and Y is

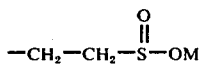

wherein M has the above definition comprises reacting a compound of formula Ia, Ib, Ic, Id or Ie with an alkali metal hydroxide or ammonium hydroxide to obtain the desired compound of formula I wherein M is an alkali metal or —NH$_4$ and if desired, reacting the latter with an acidification agent to obtain a compound of formula I wherein M is hydrogen and finally reacting the latter, if desired, with an alkali metal hydroxide to obtain the corresponding alkali metal salt.

The compounds of formulae III, IV, VI and VIII formed as intermediates in the production of compounds of formula I are novel products and are a facet of the invention.

The starting materials of formula II may be prepared by the procedure described in Belgium Pat. No. 810,644 wherein a compound of the formula

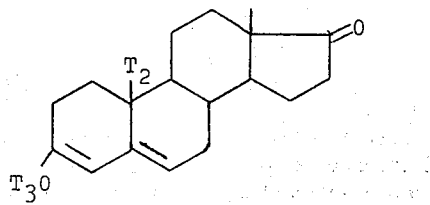

wherein T$_2$ is hydrogen or methyl and T$_3$ is methyl or ethyl is reacted in the presence of a basic agent with a trimethylsulfonium halide where the halide is bromine or iodine to obtain a compound of the formula

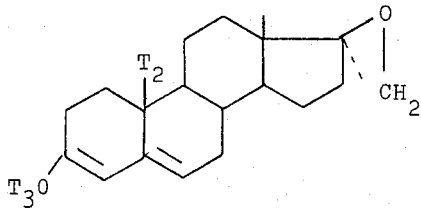

The novel compositions of the invention for antagonizing aldosterone are comprised of at least one compound of formula I and a pharmaceutical carrier. The compositions may be in the form of tablets, coated tablets, cachets, capsules, granules, emulsions, syrups, suppositories or injectable solutions or suspensions prepared in the usual way.

The pharmaceutical carrier may be any of the usual excipients such as talc, arabic gum, lactose, starch, magnesium stearate, cacao butter, aqueous or non-aqueous vehicles, fatty bodies of animal or vegetable origin, paraffinic derivatives, glycols, preservatives and diverse wetting agents, emulsifiers or dispersants.

The compositions possess an antagonistic activity against aldosterone and increase sodium excretion while conserving organic potassium. They are useful in the treatment of arterial hypertension and cardiac insufficiencies and may be used with other medicaments.

The novel method of the invention for treating arterial hypertension and cardiac insufficiency in warm-blooded animals comprises administering to warm-blooded animals an effective amount of at least one compound of formula I. The compounds may be administered orally, rectally, transcutaneously or intravenously. The usual useful daily dose is depending upon the method of administration and the particular compound. The usual useful daily dose is 2 to 20 mg/kg in the adult by oral route.

In the following examples there are described several preferred embodiments to illustrate the invention. However, it should be understood that the invention is not intended to be limited to the specific embodiments.

EXAMPLE 1

Sultine of $\Delta^4$-(17$\alpha$)-pregnene-17-ol-3-one-21-sulfinic acid (isomers A and B)

STEP A: (+) and (−) $\Delta^4$-(17$\alpha$)-pregnene-17-ol-3-one-21-tert.-butylsulfinyl 180 ml of a 2M solution n of butyllithium in cyclohexane was added at 5°C under a nitrogen atmosphere to a mixture of 43.2 g of tert.-butyl methyl sulfoxide in 650 ml of tetrahydrofuran and then 29.6 g of 3-ethoxyspiro-17$\beta$-oxiranyl-$\Delta^{3,5}$-estradiene were added. After 6 hours of reaction at room temperature, the reaction mixture was diluted with water and was extracted with ethyl acetate. The extract dissolved in 380 ml of acetone was reacted with 38 ml of concentrated hydrochloric acid diluted with 2 parts by weight of water for one hour and the resulting precipitate was washed and dried to obtain 27.65 g of a product melting at 230°–235°C. The product was chromatographed over silica gel and was eluted with a 70–30 methylene chloride-acetone mixture to obtain (−) $\Delta^4$-(17$\alpha$)-pregnene-17-ol-3-one-21-tert.-butylsulfinyl melting at 255°C and having a specific rotation $[\alpha]_D^{20} = -22.3°[c = 1\%$ in chloroform] and (+) $\alpha^4$-(17$\alpha$)-pregnene-17-ol-3-one-21-tert.-butylsulfinyl melting at 215°C and having a specific rotation $[\alpha]_D^{20} = +102.5°(c = 1\%$ in chloroform).

STEP B: sultine of $\Delta^4$-(17$\alpha$)-pregnene-17-ol-3-one-21-sulfinic acid (isomers A and B)

A solution of the product of Step A melting at 230°–235°C in 300 ml of methylene chloride was reacted with 10.5 g of N-chlorosuccinimide for 1 hour at room temperature and the resulting organic phase was washed with water and evaporated to dryness. The product was subjected to chromatography over silica gel to obtain the two diastereoisomeric sultines of $\Delta^4$-(17$\alpha$)-pregnene-17-ol-3-one-21-sulfinic acid, isomer A with a melting point of 220°C and a specific rotation $[\alpha]_D^{20} = 26.7°$ ($c = 1\%$ in ethanol) and isomer B melting at 175°–176°C and having a specific rotation $[\alpha]_D^{20} = -6.9°$ ($c = 1\%$ in ethanol).

EXAMPLE 2

Sultine of $\Delta^4$-(17α)-pregnene-17-ol-3-one-21-sulfinic acid (isomer A)

A solution of 795 mg of (+) $\Delta^4$-(17α)-pregnene-17-ol-3-one-21-tert.-butylsulfinyl in 8 ml of tetrahydrofuran and 4 ml of distilled water was reacted with 300 mg of N-chlorosuccinimide for one hour at room temperature and the reaction mixture was diluted with water. The mixture was distilled to remove tetrahydrofuran during which a crystalline product formed which was crystallized to obtain 87.5% yield of the sultine of $\Delta^4$-(17α)-pregnene-17-ol-3-one-21-sulfinic acid (isomer A) melting at 220°C.

EXAMPLE 3

Sultine of $\Delta^4$-(17α)-pregnene-17-ol-3-one-21-sulfinic acid (isomer B)

A solution of 360 mg of (−) $\Delta^4$-(17α)-pregnene-17-ol-3-one-21-tert.-butylsulfinyl in 6 ml of tetrahydrofuran and 3 ml of water was reacted with 137 mg of N-chlorosuccinimide for 30 minutes at room temperature and was then diluted with water. The tetrahydrofuran was distilled off and the product was crystallized from aqueous isopropanol to obtain a 77% yield of the sultine of α⁴-(17α)-pregnene-17-ol-3-one-21-sulfinic acid (isomer B) melting at 175°–176°C.

EXAMPLE 4

Sultine of $\Delta^{1,4}$-(17α)-pregnadiene-17-ol-3-one-21-sulfinic acid (isomer B)

STEP A: (−) $\Delta^{1,4}$-pregnadiene-17-ol-3-one-21-tert.-butylsulfinyl

A solution of 0.5 g of (−) $\Delta^4$-(17α)-pregnene-17-ol-3-one-21-tert.-butylsulfinyl (melting at 255°C) and 15 ml of methanol was added with stirring to 500 ml distilled water and 5 g of an acetonic Arthrobacter Simplex powder (UC 1047) were added to the resulting suspension and the mixture was stirred with aeration at 34°–35°C for 18 hours. The mixture was extracted with chloroform and the organic phase was decanted and evaporated to dryness. The residue was chromatographed over silica gel and was eluted with an 80-20 chloroform-acetone mixture to obtain 355 mg of $\Delta^{1,4}$-(17α)-pregnadiene-17-ol-3-one-21-tert.-butylsulfinyl with a melting point of 242°C and a specific rotation $[\alpha]_D^{20} = -60°$ ($c = 0.65\%$ in chloroform).

STEP B: Sultine of $\Delta^{1,4}$-(17α)-pregnadiene-17-ol-3-one-21-sulfinic acid (isomer B)

A solution of 1.8 g of (−) $\Delta^{1,4}$-(17α)-pregnadine-17-ol-3-one-21-tert.-butylsulfinyl in 22 ml of distilled water and 22 ml of tertrahydrofuran was cooled on an ice bath and 627 mg of N-chlorosuccinimide were added thereto. The reaction mixture was stirred at room temperature for 1 hour and was chromatographed over silica gel. Elution with a 6-4 benzene-acetone mixture yielded 1.14 g of the sultine of $\Delta^{1,4}$-(17α)-pregnadiene-17-ol-3-one-21-sulfinic acid (isomer B) melting at 180°C, then 200°C after resolidification and having a specific rotation $[\alpha]_D^{20} = -50.5°$ ($c = 1\%$ in chloroform).

EXAMPLE 5

Sultine of $\Delta^{1,4}$-(17α)-pregnadiene-17-ol-3-one-21-sulfinic acid (isomer A)

STEP A:

(+)$\Delta^{1,4}$-(17α)-pregnadiene-17-ol-3-one-21-tert.-butylsulfinyl

A solution of 2 g of (+) $\Delta^4$-(17α)-pregnene-17-ol-3-one-21-tert.-butylsulfinyl (melting at 215°C) in 40 ml of methanol was added with stirring to 2 liters of distilled water and then 10 g of acetonic powder of Arthrobacter Simplex (UC 1047) were added thereto. The suspension was aerated with air at 34°C for 2½ hours and 60 ml of methanol were added. After about 18 hours, the mixture was extracted with chloroform. The aqueous phase was decanted and evaporated to dryness to obtain 2.2 g of a resin which was chromatographed over silica gel. Elution with a 6-4 benzene-acetone mixture yielded (+) $\Delta^{1,4}$-(17α)-pregnadiene-17-ol-3-one-21-tert.-butylsulfinyl melting at 170°C and having a specific rotation $[\alpha]_D^{20} = +64°$ [$c = 0.8\%$ in chloroform].

STEP B: Sultine of $\Delta^{1,4}$-(17α)-pregnadiene-17-ol-3-one-21-sulfinic acid (isomer A)

668 mg of N-chlorosuccinimide were added to a solution of 1.9 g of the product of Step A in 23 ml of tetrahydrofuran and 23 ml of distilled water and after letting the mixture stand at room temperature for one hour, the tetrahydrofuran was distilled off under reduced pressure. The mixture was vacuum filtered and the recovered precipitate was washed with water and dried to obtain 1.13 g of sultine of $\Delta^{1,4}$(17α)-pregnadiene-17-ol-3-one-21-sulfinic acid (isomer A) melting at 175°–176°C and having a specific rotation $[\alpha]_D^{20} = -5°$ ($c = 1\%$ in chloroform).

EXAMPLE 6

Sultine of $\Delta^{4,6}$-(17α)-pregnadiene-17-ol-3-one-21-sulfinic acid (isomer B)

STEP A: Sultine of 3-ethoxy-$\Delta^{3,5}$-(17α)-pregnadiene-17-ol-21-sulfinic acid (isomer B)

0.6 ml of a solution of 50 ml of ethanol and 0.1 ml of sulfuric acid was added to a solution of 3 g of the sultine of $\Delta^4$-(17α)-pregnene-17-ol-3-one-21-sulfinic acid (isomer B melting at 175°–176°C) in 30 ml of absolute ethanol and 3 ml of ethyl orthoformate and the mixture was refluxed for 5 minutes. The mixture was neutralized with triethylamine and was diluted with water and vacuum filtered. The recovered precipitate was washed and dried to obtain 3 g of the sultine of 3-ethoxy-$\Delta^{3,5}$-(17α)-pregnadiene-17-ol-21-sulfinic acid (isomer B) melting at 192°C.

STEP B: Sultine of $\Delta^{4,6}$-(17α)-pregnadiene-17-ol-3-one-21-sulfinic acid (isomer B)

2.07 g of chloranil were added to a suspension of 3 g of the sultine of 3-ethoxy-$\Delta^{3,5}$-(17α)-pregnadiene-17-ol-21-sulfinic acid (isomer B) in 60 ml of acetone containing 5% of water and the mixture was stirred for 3½ hours and then was poured into water. The mixture was extracted with ethyl acetate and the organic phase was washed with water and evaporated to dryness to obtain after purification 2.2 g of the sultine of $\Delta^{4,6}$-(17$\alpha$)-pregnadiene-17-ol-3-one-21-sulfinic acid (isomer B) melting at 217°–218°C and having a specific rotation of $[\alpha]_D^{20} = -89.7°$ ($c = 1\%$ in chloroform).

EXAMPLE 7

Sultine of 7$\alpha$-acetylthio-$\Delta^4$-(17$\alpha$)-pregnene-17-ol-3-one-21-sulfinic acid (isomer B)

A solution of 1.23 g of the sultine of $\Delta^{4,6}$-(17$\alpha$)-pregnadiene-17-ol-3-one-21-sulfinic acid (isomer B) in 9 ml of methanol and 0.9 ml of thioacetic acid was refluxed for 1 hour and was then cooled. The mixture was vacuum filtered and the recovered precipitate was washed to obtain 1.024 g of the sultine of 7$\alpha$-acetylthio-$\Delta^4$-(17$\alpha$)-pregnene-17-ol-3-one-21-sulfinic acid (isomer B) melting at 268°C and having a specific rotation of $[\alpha]_D^{20} = 83.2°$ ($c = 1\%$ in chloroform).

EXAMPLE 8

Sultine of $\Delta^{4,6}$-(17$\alpha$)-pregnadiene-17-ol-3-one-21-sulfinic acid (isomer A)

STEP A: Sultine of 3-ethoxy-$\Delta^{3,5}$-(17$\alpha$)-pregnadiene-17-ol-21-sulfinic acid (isomer A)

A mixture of 3.3 g of the sultine of $\Delta^4$-(17$\alpha$)-pregnene-17-ol-3-one-21-sulfinic acid (isomer A melting at 220°C), 16.5 ml of absolute ethanol, 3.3 g of ethyl orthoformate and 0.6 ml of a 0.2% sulfuric acid solution in ethanol was refluxed for 5 minutes and then a few drops of triethylamine and water were added thereto. The mixture was vacuum filtered and the recovered precipitate was washed and dried to obtain, after purification, 3.08 g of the sultine of 3-ethoxy-$\Delta^{3,5}$-(17$\alpha$)-pregnadiene-17-ol-21-sulfinic acid (isomer A) melting at 176°C.

STEP B: Sultine of $\Delta^{4,6}$-(17$\alpha$)-pregnadiene-17-ol-3-one-21-sulfinic acid (isomer A)

A suspension of 2.84 g of the sultine of Step A in 28 ml of acetone, 1.4 ml of water and 1.95 g of chloranil was stirred at room temperature for 3½ hours and the mixture was extracted. The precipitate after purification was 2.06 g of the sultine of $\Delta^{4,6}$-(17$\alpha$)-pregnadiene-17-ol-3-one-21-sulfinic acid (isomer A) melting at 246°C and having a specific rotation of $[\alpha]_D^{20} = -41°$ ($c = 1\%$ in chloroform).

EXAMPLE 9

Sultine of 7$\alpha$-acetylthio-$\Delta^4$-(17$\alpha$)-pregnene-17-ol-3-one-21-sulfinic acid (isomer A)

A suspension of 1.84 g of the sultine of $\Delta^{4,6}$-(17$\alpha$)-pregnadiene-17-ol-3-one-21-sulfinic acid (isomer A) in 15 ml of methanol and 1.5 ml of thioacetic acid was heated for 1½ hours with stirring to obtain 2.4 g of a precipitate which was purified to obtain 1.71 g of the sultine of 7$\alpha$-acetylthio-$\Delta^4$-(17$\alpha$)-pregnene-17-ol-3-one-21-sulfinic acid (isomer A) melting at 234°C and having a specific rotation of $[\alpha]_D^{20} = -49°$ ($c = 0.8\%$ in chloroform).

EXAMPLE 10

Sultine of 19-nor-$\Delta^4$-(17$\alpha$)-pregnene-17-ol-3-one-21-sulfinic acid (isomer A)

STEP A: (+) and (−)19-nor-$\Delta^4$-(17$\alpha$)-pregnene-17-ol-3-one-21-tert.-butylsulfinyl 28.8 g of methyl tert.-butyl sulfoxide were added under a nitrogen atmosphere with stirring to 300 ml of anhydrous tetrahydrofuran and after cooling the mixture to 0°C, 120 ml of a 20% solution of butyllithium in cyclohexane were added thereto over 45 minutes. Then, 18.75 g of 3-ethoxy-spiro-17$\beta$-oxiranyl-$\Delta^{3,5}$-androstadiene were added thereto and the mixture stood at room temperature for 4 hours. The reaction mixture was poured into a mixture of water and hydrochloric acid and was then extracted. The extracts were washed with water and evaporated to dryness to obtained 31.6 g of a resin which was then added to 100 ml of acetone and 20 ml of N hydrochloric acid. After 20 minutes, the mixture was diluted with water and the recovered precipitate weighing 24.4 g was chromatographed over silica gel. Elution with a 7-3 methylene chloride-acetone mixture gave 7.5 g of (−) 19-nor-$\Delta^4$-(17$\alpha$)-pregnene-17-ol-3-one-21-tert.-butylsulfinyl melting at -one-tert.-butylsulfinyl −240°C and having a specific rotation of $[\alpha]_D^{20} = -68°$ ($c = 1.4\%$ in chloroform) and 6.370 g of (+) 19-nor-$\Delta^4$-(17$\alpha$)-pregnene-17-ol-3-one-tert.-butylsufinly melting at 196°C and having a specific rotation of $[\alpha]_D^{20} = +63.5$ ($c = 1.4\%$ in chloroform).

STEP B: Sultine of 19-nor-$\Delta^4$-(17$\alpha$)-pregnene-17-ol-3-one-21-sulfinic acid (isomer A)

50 ml of water were added to a suspension of 4.06 g of (+) 19-nor-$\Delta^4$-(17$\alpha$)-pregnene-17-ol-3-one-21-tert.-butylsulfinyl melting at 190°C in 25 ml of tetrahydrofuran and 1.42 g of N-chlorosuccinimide were added to the resulting solution. After 30 minutes of reacting, 50 ml of water were added and the mixture was vacuum filtered. The precipitate was washed and dried to obtain, after purification, 3.01 g of the sultine of 19-nor-$\Delta^4$-(17$\alpha$)-pregnene-17-ol-3-one-21-sulfinic acid (isomer A) melting at 236°–238°C and having a specific rotation of $[\alpha]_D^{20} = -23.5°$ ($c = 0.50\%$ in chloroform).

EXAMPLE II

Sultine of 19-nor-$\Delta^4$-(17$\alpha$)-pregnene-17-ol-3-one-21-sulfinic acid (isomer B)

340 mg of N-chlorosuccinimide were added to a solution of 945 mg of (−) 19-nor-$\Delta^4$-(17$\alpha$)-pregnene-17-ol-3-one-21-tert.-butylsulfinyl melting at 239°–240°C in 112.5 ml of tetrahydrofuran and 11.25 ml of water and the reaction mixture was stirred for one hour and then evaporated to dryness under reduced pressure. The residue was purified to obtain 775 mg of the sultine of 19-nor-$\Delta^4$-(17$\alpha$)-pregnene-17-ol-3-one-21-sulfinic acid (isomer B) melting at 194°C and having a specific rotation of $[\alpha]_D^{20} = -45.5°$ ($c = 0.8\%$ in chloroform).

EXAMPLE 12

Sultine of 19-nor-Δ⁴·⁶-(17α)-pregnadiene-17-ol-3-one-21-sulfinic acid (isomer B)

A mixture of 3.34 g of the sultine of 19-nor-Δ⁴-(17α)-pregnene-17-ol-3-one-21-sulfinic acid (isomer B), 16 ml of absolute ethanol, 3.3 ml of ethyl orthoformate and 0.6 ml of a solution of 0.2% sulfuric acid in ethanol was refluxed for 5 minutes and then 1 ml of triethylamine was added thereto. The mixture was cooled and extracted to obtain 4.2g of a residue which was added to a mixture of 80 ml of acetone, 4 ml of water and 2.59 g of chloranil. The suspension was stirred for 2 hours at room temperature to obtain, after purification, 2.35 g of the sultine of 19-nor-Δ⁴·⁶-(17α)-pregnadiene-17-ol-3-one-21-sulfinic acid (isomer B) melting at 268°C and having a specific rotation of $[\alpha]_D^{20} = -150°$ ($c = 1\%$ in chloroform).

EXAMPLE 13

Sultine of 19-nor-Δ⁴·⁶-(17α)-pregnadiene-17-ol-3-one-21-sulfinic acid (isomer A)

STEP A: Sultine of 3-ethoxy-19-nor-Δ³·⁵-(17α)-pregnadiene-17-ol-21-sulfinic acid (isomer A)

A suspension of 1.82 g of the sultine of 19-nor-Δ⁴-(17α)-pregnene-17-ol-3-one-21-sulfinic acid (isomer A melting at 236°-238°C) in 18 ml of absolute ethanol and 1.8 ml of ethyl orthoformate and 9 mg of p-toluene sulfonic acid monohydrate was stirred at room temperature and dissolution occured after 15 minutes followed by crystallization of the enolic ether. After 3 hours, the mixture was neutralized with 0.5 ml of triethylamine and was diluted with water and vacuum filtered to obtain 1.42 g of the sultine of 3-ethoxy-19-nor-Δ³·⁵-(17α)-pregnadiene-17-ol-21-sulfinic acid (isomer A) melting at 170°C.

STEP B: Sultine of 19-nor-Δ⁴·⁶-(17α)-pregnadiene-17-ol-3-one-21-sulfinic acid (isomer A)

A suspension of 1.42 g of the sultine of Step A, 1.02 g of chloranil, 28 ml of acetone and 1.4 ml of water was stirred at room temperature for 4½ hours and the precipitate was purified by chromatography over silica gel and was crystallized from isopropanol to obtain the sultine of 19-nor-Δ⁴·⁶-(17α)-pregnadiene-17-ol-3-one-21-sulfinic acid (isomer A) melting at 196°C and having a specific rotation of $[\alpha]_D^{20} = -117.5°$ ($c = 0.7\%$ in chloroform).

EXAMPLE 14

Δ⁴-(17α)-pregnene-17-ol-3-one-21-sulfinic acid 80 ml of N sodium hydroxide solution were added to a suspension of 2.45 g of the sultine of Δ⁴-(17α)-pregnene-17-ol-3-one-21-sulfinic acid (isomer A or B) in 100 ml of absolute ethanol and after dissolution occured, the reaction mixture was allowed to stand at room temperature for 2 hours. The mixture was concentrated by distilling off the ethanol and was then acidified with 20 ml of N sulfuric acid and filtered to obtain a precipitate which after crystallization from methanol and water yielded 1.93 g of Δ⁴-(17α)-pregnene-17-ol-3-one-21-sulfinic acid monohydrate with a specific rotation $[\alpha]_D^{20} = +49°$ ($c$ in 0.1 N sodium hydroxide).

EXAMPLE 15

Potassium Δ⁴-(17α)-pregnene-17-ol-3-one-21-sulfinate

A solution of 475 mg of Δ⁴-(17α)-pregnene-17-ol-3-one-21-sulfinic acid in 5 ml of isopropanol and 1.05 ml of 1.2 N methanolic potassuim hydroxide was concentrated to dryness and the residue was crystallized from isopropanol containing 10% water. The mixture was vacuum filtered and the precipitate was washed and dried in air to obtain 330 mg of potassium Δ⁴-(17α)-pregnene-17-ol-3-one-21-sulfinate in the form of hydrated crystals containing about 12% water.

EXAMPLE 16

Tablets were prepared containing 50 mg of the product of Example 6 and excipient of talc, starch and magnesium stearate.

PHARMACOLOGICAL DATA

A. Antialdosterone activity in rats

Male rats of the Sprague Dawley strain weighing about 180 g were subjected to surrenalectomy and at this moment, the rats received a drink of physiological serum. After 31 hours, the animals were fasted and then received a drink of an aqueous 5% glucose solution. After 47 hours, the product of Examples 6, 9, 7 or 13 were orally administered in suspension or in solution in an aqueous 0.25% carboxymethylcellulose solution. After 48 hours or 1 hour after the oral administration of the products, the rats received on the one hand intraperitoneally a hydrosaline surcharge at a dose of 5 ml/100 g of body weight of a 9% physiological serum and on the other hand subcutaneously 1 μg/kg of the monoacetate of aldosterone in a 2.5% alcoholic solution. The rats were placed in diuresis cages without food or drink for 4 hours. After this time, a forced urination was effected by pressure on the bladder and the volume of urine obtained was adjusted to 50 ml and the amounts of sodium and potassium present therein was determined by an autoanalyzer. The results are expressed as a percentage of inhibition of the activity of 1 μg/kg of the subcutaneously injected monoacetate of aldosterone by the ratio of sodium concentration to potassium concentration of the surrenalectomized rats. The results are in Table I.

TABLE I

| Product of Example | Dose in mg/kg orally administered | % of inhibition |
|---|---|---|
| 6 | 5 | 30 |
| 9 | 10 | 36 |
| 7 | 5 | 24 |
| 13 | 5 | 24 |

Various modifications of the products and methods of the invention without departing from the spirit or scope thereof and it is to be understood that the invention is intended to be limited only as defined in the appended claims.

We claim:
1. A compound of the formula

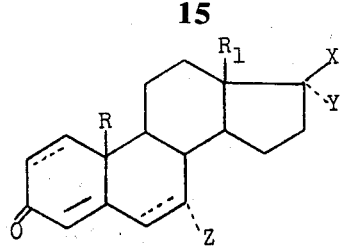

wherein R is selected from the group consisting of hydrogen and methyl, $R_1$ is alkyl of 1 to 4 carbon atoms, Z is selected from the group consisting of hydrogen and

of α-configuration, $R_2$ is alkyl of 1 to 4 carbon atoms, the dotted lines in the A and B rings represent optional 1 or 2 double bonds in the 1(2) position when R is methyl and in the 6(7) position when Z is hydrogen and X and Y together form the group

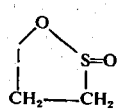

and when X is OH, Y is

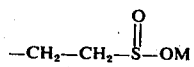

and M is selected from the group consisting of hydrogen, $-NH_4$ and alkali metals.

2. A compound of claim 1 wherein $R_1$ is methyl.

3. A compound of claim 1 wherein X and Y together form

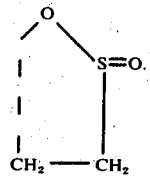

4. A compound of claim 1 wherein Y is

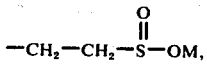

M is selected from the group consisting of hydrogen, $-NH_4$ and alkali metal and X is OH.

5. A compound of claim 3 wherein Z is hydrogen and there is only a double bond in the 4(5) position.

6. A compound of claim 3 wherein Z is hydrogen and there are 2 double bonds in the 1(2) and 4(5) positions.

7. A compound of claim 3 wherein Z is hydrogen and there are 2 double bonds in the 4(5) and 6(7) positions.

8. A compound of claim 1 wherein Z is

and there is a double bond in the 4(5) position only.

9. A compound of claim 4 wherein M and Z are hydrogen and there is a double bond in the 4(5) position only.

10. A compound of claim 1 which is the diastereoisomeric sultine of $\Delta^4$-(17α)-pregnene-17-ol-3-one-21-sulfinic acid.

11. A compound of claim 1 which is the diastereoisomeric sultine of 19-nor-$\Delta^4$-(17α)-pregnene-17-ol-3-one-21-sulfinic acid.

12. A compound of claim 1 which is the diastereoisomeric sultine of $\Delta^{1,4}$-(17α)-pregnadiene-17-ol-3-one-21-sulfinic acid.

13. A compound of claim 1 which is the diastereoisomeric sultine of $\Delta^{4,6}$-(17α)-pregnadiene-17-ol-3-one-21-sulfinic acid.

14. A compound of claim 1 which is the diastereoisomeric sultine of 7α-acetylthio-$\Delta^4$-(17α)-pregnene-17-ol-3-one-21-sulfinic acid.

15. A compound of claim 1 which is the diastereoisomeric sultine of 19-nor-$\Delta^{4,6}$-(17α)-pregnadiene-17-ol-3-one-21-sulfinic acid.

16. A compound of claim 1 which is $\Delta^4$-(17α)-pregnene-17-ol-3-one-21-sulfinic acid.

17. A compound of claim 1 which is potassium $\Delta^4$-(17α)-pregnene-17-ol-3-one-21-sulfinate.

18. A compound of the formula

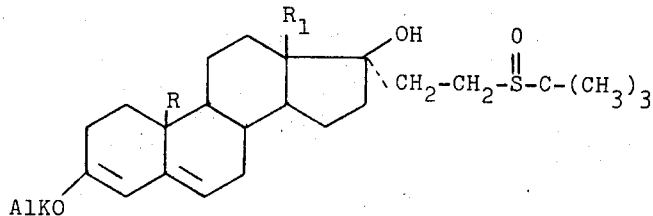

wherein R is selected from the group consisting of hydrogen and methyl and AlK and $R_1$ are alkyl of 1 to 4 carbon atoms.

19. A compound of the formula

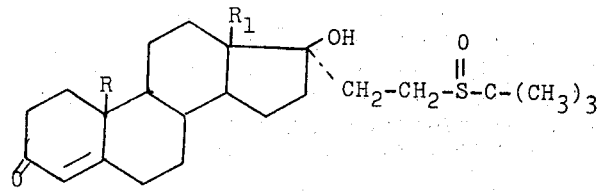

wherein R is selected from the group consisting of hydrogen and methyl and $R_1$ is alkyl of 1 to 4 carbon atoms.

20. A compound of the formula

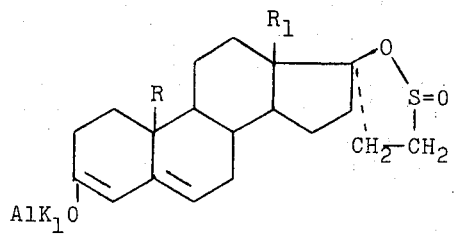

wherein R is selected from the group consisting of hydrogen and methyl and $R_1$ and $AlK_1$ are alkyl of 1 to 4 carbon atoms.

21. A compound of the formula

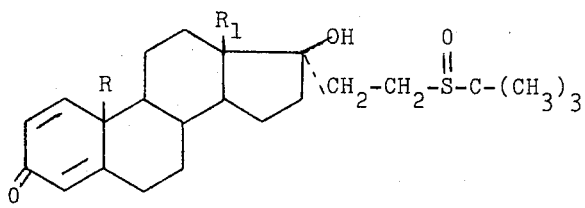

wherein R is selected from the group consisting of hydrogen and methyl and $R_1$ is alkyl of 1 to 4 carbon atoms.

22. A composition for treating arterial hypertension and cardiac insufficiency comprising an effective amount of at least one compound of claim 1 and a pharmaceutical carrier.

23. A method for the treatment of arterial hypertension and cardiac insufficiency in warm-blooded animals comprising administering to warm-blooded animals at least one compound of claim 1 in an amount effect to reduce arterial hypertension and overcome cardiac insufficiency.

24. The method of claim 23 wherein the compound is the sultine of $\Delta^{4,6}$-(17α)-pregnadiene-17-ol-3-one-21-sulfinic acid (isomer B).

* * * * *